United States Patent [19]

Dessau et al.

[11] Patent Number: 4,935,566
[45] Date of Patent: Jun. 19, 1990

[54] DEHYDROCYCLIZATION AND REFORMING PROCESS

[75] Inventors: Ralph M. Dessau, Edison; Randall D. Partridge, W. Trenton, both of N.J.; Ernest W. Valyocsik, Yardley; James C. Vartuli, West Chester, both of Pa.

[73] Assignee: Mobil Oil Corporation, New York, N.Y.

[21] Appl. No.: 295,954

[22] Filed: Jan. 11, 1989

Related U.S. Application Data

[63] Continuation-in-part of Ser. No. 210,948, Jun. 24, 1988, abandoned, which is a continuation-in-part of Ser. No. 211,207, Jun. 24, 1988, abandoned, which is a continuation-in-part of Ser. No. 210,963, Jun. 24, 1988, abandoned, which is a continuation-in-part of Ser. No. 230,729, Aug. 5, 1988, abandoned, which is a continuation of Ser. No. 122,089, Nov. 17, 1987, abandoned.

[51] Int. Cl.$^5$ .................. C10G 35/06; C07C 2/52
[52] U.S. Cl. ..................... 208/65; 208/138; 585/419
[58] Field of Search ............... 208/65, 138; 585/419

[56] References Cited

U.S. PATENT DOCUMENTS

| | | | |
|---|---|---|---|
| Re. 29,948 | 3/1979 | Dwyer et al. | 208/110 |
| 3,702,293 | 11/1972 | Hayes et al. | 208/139 |
| 3,702,294 | 11/1972 | Rausch | 208/139 |
| 3,878,125 | 4/1975 | Mitsche et al. | 502/73 |
| 3,878,131 | 4/1975 | Hayes | 252/466 PT |
| 4,104,320 | 8/1978 | Bernard et al. | 260/673.5 |
| 4,276,151 | 6/1981 | Plank et al. | 208/138 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,478,706 | 10/1984 | Cohen | 585/419 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,634,518 | 1/1987 | Buss et al. | 208/138 |
| 4,737,262 | 4/1988 | Franck et al. | 208/65 |

FOREIGN PATENT DOCUMENTS

0107389  4/1984  European Pat. Off.
2033358  5/1980  United Kingdom.
2114150  8/1983  United Kingdom.

OTHER PUBLICATIONS

G. Wengui et al "IR Study of Framework Vibrations and Surface Properties of High Silica Zeolites", ZEO-LITES, Elsevir Science, Amsterdam, 1985, p. 279.

Ione, Journal of Molecular Cataysis, 31, pp. 355–370 (1985).

Ione, "Structure and Reactivity of Modified Zeolites", ELSEVIR Science, (1984), pp. 151–155.

Huagong, vol. 15, No. 7 (1986) (with translation).

*Primary Examiner*—Curtis R. Davis
*Attorney, Agent, or Firm*—Alexander J. McKillop; Charles J. Speciale; Marina V. Schneller

[57] ABSTRACT

An improved, low-pressure dehydrocyclization and/or reforming process based on a non-acidic metal containing crystalline microporous tin catalyst, in which the feed is rich in low octane hydrocarbons, such as paraffins, and in which the product has increased aromatic content and increased octane value over that of the feed.

75 Claims, 1 Drawing Sheet

EFFECT OF INERT DILUENT

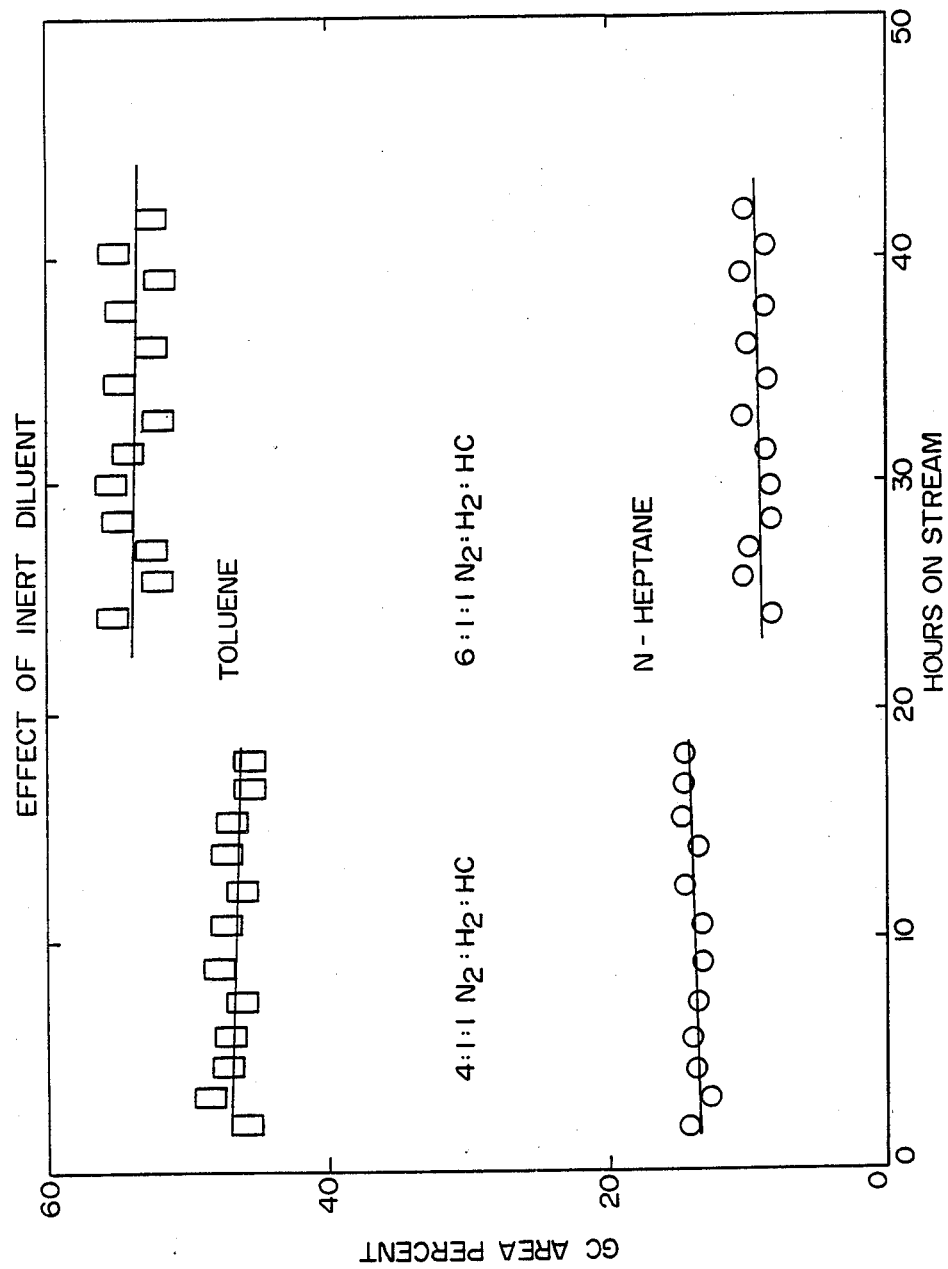

DEHYDROCYCLIZATION AND REFORMING PROCESS

CROSS REFERENCE TO RELATED APPLICATIONS

This application is a continuation-in-part of Ser. No. 210,948 filed June 24, 1988, of Ser. No. 211,207 filed June 24, 1988, of Ser. No. 210,963 filed June 24, 1988 and of Ser. No. 230,729 filed Aug. 5, 1988, which in turn is a continuation of Ser. No. 122,089 filed Nov. 17, 1987. Each of said applications is now abandoned and is relied upon and incorporated by reference herein.

FIELD OF THE INVENTION

This invention relates to the manufacture of benzene and toluene from normal hexane and normal heptane.

The invention also relates to catalytic reforming of naphthas having low octane values to increase that octane value. The catalyst comprises a non-acidic platinum-tin containing crystalline microporous material. A result of the catalytic process of the invention is an increase in liquid yields by minimizing, if not eliminating, the cracking of $C_5+$ hydrocarbons such as $C_6$ and $C_7$ paraffins.

The invention is directed to improving reforming to maximize yields and octane increase of the reformate. The improvements are realized by decreasing the partial pressure of hydrogen, an off gas or byproduct of reforming, in the reforming unit and employing as the reforming catalyst, a non-acidic tin containing crystalline microporous material combined with a reforming hydrogenation/dehydrogenation metal, such as platinum. The invention also relates to catalytic treatment of a reformate high in $C_5+$ paraffin content and of low octane. The catalyst used is a non-acidic tin containing crystalline microporous material, containing a hydrogenation/dehydrogenation metal. That $C_5+$ paraffin component of the feed is converted to aromatic components of higher octane value thereby increasing the octane rating of the reformate.

BACKGROUND OF THE INVENTION

Very large amounts of benzene and toluene are consumed annually. These materials find use as chemical intermediates, solvents, and in gasoline.

By far the largest proportion of the available benzene and toluene is made in petroleum refining by the so-called (petroleum naphtha) reforming process. This process is so well known that it need not be described in detail here. Briefly, one of the major reactions in catalytic reforming is the isomerization and dehydrogenation of five and six-membered naphthene compounds contained in the naphtha to form a mixture of benzene, toluene, and xylene which materials can be recovered by distillation and solvent extraction as a mixture commonly referred to as "BTX". This mixture can be resolved by distillation to provide merchant benzene, toluene, and mixed xylenes for further use.

The statutory elimination of lead from most gasolines has compelled refiners to rely heavily on hydrocarbon conversion processes that produce gasoline blending stocks having a high octane number even without the inclusion of lead. Two principal processes for accomplishing this are alkylation and reforming, which produce such high octane blending stocks for the lead-free gasolines. Accordingly, refiners who rely heavily on reforming for gasoline production are understandably reluctant to allow the reformate product to be stripped of the high octane aromatics. There results from this situation a decrease in the available supply of benzene and toluene and a concomitant increase in their cost. There is an evident growing need for alternative methods to manufacture benzene and toluene, methods which do not rely on reformate as the principal source.

Catalytic reforming is a process in which hydrocarbon molecules are rearranged, or reformed in the presence of a catalyst. The molecular rearrangement results in an increase in the octane ring of the feedstock. Thus, during reforming low octane hydrocarbons in the gasoline boiling range are converted into high octane components by dehydrogenation of naphthenes and isomerization, dehydrocyclization and hydrocracking of paraffins.

A reformate is the product of the reforming process. The importance of reforming is reflected by data which indicates that finished pool gasoline is about 35% reformate in complex refineries, but can run as high as 80% in topping-reforming refineries. As lead is phased out of gasoline, more and more straight run stocks which are now blended directly into gasoline will be reformed. All current commercial reformers use a platinum containing catalyst with a hydrogen recycle stream.

By way of illustration, the significance of those reactions in reforming can be gleaned from a review of the following table from "Catalysis," vol VI, P. H. Emmett (ed). Copyright 1958 by Litton Educational Publishing Company:

| Octane Numbers of Pure Hydrocarbons | |
|---|---|
| Hydrocarbon | Blending research octane number (clear) |
| Paraffins: | |
| n-Butane | 113 |
| n-Pentane | 62 |
| n-Hexane | 19 |
| n-Heptane | 0 |
| n-Octane | −19 |
| 2-Methylhexane | 41 |
| 2,2-Dimethylpentane | 89 |
| 2,2,3-Trimethylbutane | 113 |
| Naphthenes (cycloparaffins): | |
| Methylcyclopentane | 107 |
| 1.1-Dimethylcyclopentane | 96 |
| Cyclohexane | 110 |
| Methylcyclohexane | 104 |
| Ethylcyclohexane | 43 |
| Aromatics: | |
| Benzene | 99 |
| Toluene | 124 |
| 1,3-Dimethylbenzene | 145 |
| Isopropylbenzene | 132 |
| 1,3,5-Trimethylbenzene | 171 |

Naphtha reforming may also be utilized for the production of benzene, toluene, ethylbenzene, and xylene aromatics. A valuable by-product of naphtha reforming is hydrogen, which may be utilized for hydrotreating and upgrading of other hydrocarbon fractions. Generally, the molecular rearrangement of molecular components of a feed, which occurs during reforming, results in only slight, if any, changes in the boiling point of the reformate (the product of reforming), compared to that of the feed. Accordingly, reforming differs from both cracking and alkylation, both refinery processes, each of which does result in changes of boiling range of the product compared to the feed. That is, in cracking, large molecules are cracked into smaller ones; whereas, in alkylation small molecules are rebuilt into larger molecules.

The most important uses of the reforming process are briefly mentioned: the primary use of catalytic reforming may be concisely stated to be an octane upgrader and a route to premium gasoline. Catalytic reforming is the only refining process that is capable of economically making a gasoline component having high clear research octane ratings. The charge to the reformer (straight-run, thermal, or hydrocracker naphtha) is usually available in large quantities and is of such low quality that most of it would be unsaleable without reforming.

A correlative use of catalytic reforming is in its ability to produce gasolines of acceptable volatility over a wide range of yields, through proper selection of feedstock and/or operating conditions. The refiner is thus able to vary the yield of gasoline very substantially to meet demand fluctuations. For European demand patterns, where gasoline sales are limited and it is desired to produce as much middle distillate as practicable, the reformer can be operated to minimize gasoline production while maintaining high crude runs.

Hydrogen, although often considered a by-product, is still a valuable output from the reformer. Normally, it is produced in amounts ranging from 300 to 1200 SCF/Bbl, depending on the type of feed stock and reformer operating conditions. Reformer hydrogen is used to remove unwanted contaminants from reformer feed stocks, for hydrodesulfurization of distillates, hydrocracking of heavy fractions, hydrotreating of lubes and various chemical operations. Hydrogen availability and utilization is expected to assume increasing importance as pollution restrictions lead to increasing hydroprocessing in future years.

The importance of reforming is reflected by data which indicates that finished pool gasoline is about 35% reformate in complex refineries, but can run as high as 80% in topping-reforming refineries. As lead is phased out of gasoline, more and more straight run stocks which are now blended directly into gasoline will be reformed. All current commercial reformers use a platinum containing catalyst with a hydrogen recycle stream. Within this broad definition, there are a great number of different process designs. More than 75% of the industry's reforming capacity is classified as semi-regenerative. A semi-regenerative reformer is one which runs until the catalyst is coked and then is shut down and regenerated. The time period between regenerations varies from several months to as long as 1-½ years.

Within the category of semi-regenerative reforming, a further breakdown can be made on the basis of operating pressure. Units with separator pressures of 450 psig or higher are considered high pressure units. Those with pressures of 300 psig or less are called low pressure units. Anything in between is intermediate pressure. Most of the older units are high pressure, while the newer designs are low or intermediate pressure. Lower pressures given better reformate yields at a given octane level.

Another type of reformer is the cyclic variety. A cyclic unit has the reactors manifolded in such a way that any reactor can be taken out of reforming service and regenerated while the other reactors are still reforming. The time period between regenerations for a cyclic reactor varies from 2 to 10 days. All cyclics are low pressure.

A third type of reformer that has recently been commercialized is the continuous unit. In this type of reformer, catalyst is withdrawn from the unit during reforming, regenerated in small batches in separate regeneration facilities and then replaced in the unit. The regeneration period for continuous units is about one month. As in the case for cyclic units, all continuous units are low pressure.

Prior to about 1950 chromium oxide or molybdenum oxide supported on alumina were used to effect the two functions of a reforming catalyst. The hydrogenation-dehydrogenation function for paraffin olefin conversion during reforming is effected by the metals chromium and molybdenum and more recently platinum, rhenium, admixtures thereof and noble-metal containing trimetallic alloys. Isomerization activity was provided by acidified alumina.

From the commercialization of platinum reforming in the middle 1950's to the late 1960's, there was no significant improvements in reforming catalysts.

In the late 1960's a dramatic breakthrough in reforming catalysts occurred. This was the introduction of the platinum-rhenium bimetallic catalysts. These catalysts have greatly improved stability compared to platinum-only catalysts. By way of background, the platinum and platinum bimetallic catalysts were generally supported on carriers.

Recently, the patent literature has started to recognize the use of platinum and non-shape selective zeolite containing catalyst compositions in reforming. For example, that is the zeolite may replace in whole or in part the function of alumina in prior reforming catalysts. U.S. Pat. No. 4,456,527 describes zeolite L as a component in a composition for catalyzing reforming.

Zeolites include naturally occurring and synthetic zeolites. They exhibit catalytic properties for various types of hydrocarbon conversions. Zeolites are porous crystalline aluminosilicates having definite crystalline structure as determined by X-ray diffraction studies. Such zeolites have pores of uniform size which are uniquely determined by unit structure of the crystal. The zeolites are referred to as "molecular sieves" because interconnecting channel systems created by pores of uniform pore size allow a zeolite to selectively absorb molecules of certain dimensions and shapes.

By way of background, one authority has described the zeolites structurally, as "framework" aluminosilicates which are based on an infinitely extending three-dimensional network of $AlO_4$ and $SiO_4$ tetrahedra linked to each other by sharing all of the oxygen atoms. Furthermore, the same authority indicates that zeolites may be represented by the empirical formula $$M_{2/n}O.Al_2O_3.xSiO_2.yH_2O$$

In the empirical formula, x is equal to or greater than 2, since $AlO_4$ tetrahedra are joined only to $SiO_4$ tetrahedra, and n is the valence of the cation designated m. D. Breck, ZEOLITE MOLECULAR SIEVES, John Wiley & Sons, New York p. 5 (1974). In the empirical formula, the ratio of the total of silicon and aluminum atoms to oxygen atoms is 1:2. M was described therein to be sodium, potassium, magnesium, calcium, strontium and/or barium, which complete the electrovalence makeup of the empirical formula.

The prior art describes a variety of synthetic zeolites. These zeolites have come to be designated by letter or other convenient symbols, as illustrated by the zeolite ZSM-5. The silicon/aluminum atomic ratio of a given zeolite is often variable. Moreover, in some zeolites, the upper limit of the silicon/aluminum atomic ratio is unbounded. ZSM-5 is one such example wherein the silicon/aluminum atomic ratio is at least 2.5 and up to infinity. U.S. Pat. No. 3,941,871, reissued as RE. 29,948, discloses a porous crystaline silicate made from a reaction mixture containing no deliberately added aluminum and exhibiting the X-ray diffraction pattern characteristic of ZSM-5. Various patents describe inclusion of elements other than silicon and aluminum in the preparation of zeolites. Cf. U.S. Pat. No. 3,530,064, U.S. Pat. Nos. 4,208,305 and 4,238,318 describe the preparation of silicates in the presence of iron.

Zeolites may be classified by pore size. ZSM-5 is a member of a class of zeolites sometimes referred to as medium pore zeolites. The pore sizes of medium pore zeolites range from about 5 to about 7 Angstroms.

Another class of zeolites sometimes referred to as large pore zeolites include inter alia naturally occurring faujasite, synthetic zeolites X, L, Y and zeolite beta. These zeolites are characterized by pore sizes greater than those of the medium pore zeolites. The pore sizes of large pore zeolites are greater than about 7 Angstroms. Because of the larger pore sizes these latter zeolites may be less (molecule) shape selective.

SUMMARY OF THE INVENTION

The invention provides a process for manufacturing benzene, toluene, or mixtures thereof which comprises contacting under dehydrocyclization conditions a feed comprising substantially isomer-free normal hexane or normal heptane or a mixture thereof with a non-acidic dehydrocyclization catalyst comprising a platinum group metal, a crystalline microporous silicate isostructural with a tin modifier.

Naphthas, rich in $C_6$ and $C_7$ paraffins, difficult to reform selectively using conventional catalysts, are reformed over compositions containing a reforming metal and crystalline microporous non-acidic tin containing materials. The reformate produced thereby is characterized by higher net yield of aromatic gasoline than would result from reforming in the presence of conventional reforming catalysts. Moreover, products of reforming in accordance with the invention contain reduced $C_3+C_4$ fractions.

The invention also relates to improvements in reforming naphthas in the presence of a new reforming catalyst comprising a reforming metal and a non-acidic crystalline microporous material containing tin by decreasing the hydrogen partial pressure in the reforming unit. This is accomplished by the introduction of a diluent stream to reduce the hydrogen partial pressure throughout the reactor.

In accordance with the invention, a low octane severity reformate feedstock is contacted with a catalyst comprising a hydrogenation/dehydrogenation component and a non-acidic tin containing microporous crystalline material capable of converting $C_6+$ paraffins in the feedstock to $C_6+$ aromatics.

In one embodiment of the invention a naphtha feedstock is subjected to reforming conditions effective to produce a reformate having a research octane of 50 to 90, and then that reformate of 50-90 research octane is contacted with the catalyst comprising the hydrogenation/dehydrogenation component and said non-acidic tin containing microporous crystalline material, under conditions to effect the aromatization of the paraffins in the feedstock to increase the treated reformate's octane value.

This two stage process will result in overall increased liquid yields, compared to conventional reforming processes run to a given octane which result in cracking (or hydrocracking) of the $C_6+$ paraffins.

DESCRIPTION OF THE DRAWING

The figure is a graph of product toluene produced plotted as hours on stream at different diluent ratios.

DETAILED DESCRIPTION OF THE INVENTION

The Feedstocks

The feed for the process of this invention which relates to benzene and toluene production comprises substantially isomer-free normal hexane or normal heptane or mixtures thereof. The phrase "isomer-free" as used herein means free of isomeric paraffins, e.g., isomer-free normal hexane would be substantially free of 2-methyl and 3-methylpentane, and also free of 2,2-dimethyl and 2,3-dimethyl butane.

The substantially isomer-free normal hexane or normal heptane is obtainable from a distillation cut of natural gasoline. Suitable methods for separating the normal paraffins such as superfractionation, urea adduction, and bulk separation by Type 5A molecular sieve may be used. Such methods are known and need not be described herein in detail. The preferred method for use in this invention is molecular sieve separation. Several such processes are in commercial use for the recovery of normal paraffins from refinery streams. During the adsorption step of such separation, the effluent contains isoparaffins and cyclic hydrocarbons. High purity normal paraffins are recovered by desorption or by displacement with a lighter normal paraffin such as propane. Not more than about 5 wt%, and preferably not more than 2.5 wt%, of isoparaffins and cyclic compounds should be present in the feed. The normal hexane, heptane or mixture thereof should constitute at least about 90 wt% of the total $C_5+$ hydrocarbons in the feed, and preferably about 95 wt%. The normal hexane, heptane or mixture thereof is recovered by Type 5A molecular sieve separation using propane as desorbent, and the desorbed effluent containing propane is catalytically converted without prior separation of propane. Reduction of the partial pressure of the benzene and/or toluene product by propane favors its formation. For purposes of the present invention, in addition to the normal paraffins, the feed may contain a diluent such as hydrogen, an inert gas such as nitrogen, or an aliphatic hydrocarbon containing less than five carbon atoms. It is a feature of this invention that the conversion takes place with high selectivity and slow catalyst aging even in the absence of added hydrogen. However, the presence of a small amount of hydrogen may be used to further slow the aging, but some loss of catalyst activity may accompany its use. When hydrogen is used, it is preferred that it be used in conjunction with an inert gas or other hereinabove described diluent.

The use of normal hexane and normal heptane substantially free of isomers, and a feed substantially free of cyclic compounds such as methyl and dimethyl cyclopentane fosters long catalyst life and relatively infrequent regeneration.

The feedstock charge to the new reforming process can be straight-run, thermal, or catalytically cracked naphtha. Typically, naphthas boil at 80° to 400° F. Preferably, for high increases in the aromatic content and high octane numbers of the reformate, the charge to the reformer is a naphtha rich in paraffins; these are generally difficult to reform selectively using conventional catalysts (such as chlorided Pt-alumina).

Naphtha fractions boiling below 150° F., which contain pentanes and methylpentanes, are preferably taken as gasoline by blending or processed separately. The higher boiling fractions, for example, 150°–400° F. which contain $nC_6+$ paraffins are processed at reforming conditions over the catalyst used in this invention. In another embodiment, this naphtha is separated into fractions, at least one of which is processed.

For example, the 180°–250° F. light naphtha fraction containing $C_6$–$C_7$ paraffins is processed over the platinum/tin containing catalyst. This light naphtha fraction is difficult to convert selectively to aromatics over traditional dual functional reforming catalysts, where paraffin isomerization and hydrocracking reactions compete. The remaining 250° F. fraction can be processed over conventional reforming catalyst with yield and/or octane gains greater than that obtained by conventional reforming alone.

The naphtha fractions may be hydrotreated prior to reforming; but hydrotreating is not necessarily required when using the catalyst in accordance with the invention.

Initial hydrotreating of a hydrocarbon feed serves to convert sulfur, nitrogen and oxygen derivatives of hydrocarbon to hydrogen sulfide, ammonia, and water while depositing metal contaminant from hydrodecomposition of any organo-metal compounds. Where desired, interstage processing of the effluent from the hydrotreating zone may be effected. Such interstage processing may be undertaken, for example, to provide additional hydrogen, to add or remove heat or to withdraw a portion of the hydrotreated stream for treatment which need not be reformed. Hydrotreating of the heavy naphtha fraction may be essential, prior to reforming in a conventional reforming process. Suitably, the temperature in the hydrotreating catalyst bed will be within the approximate range of 550° F. to 850° F. The feed is conducted through the bed at an overall space velocity between about 0.1 and about 10 and preferably between about 0.2 and about 2, with hydrogen initially present in the hydrotreating zone in an amount between about 1000 and 10,000 standard cubic feet per barrel of feed, corresponding to a ratio of between about 2.4 and about 24 moles of hydrogen per mole of hydrocarbon.

The catalyst may be any of the known hydrotreating catalysts, many of which are available as staple articles of commerce. These hydrotreating catalysts are generally metals or metal oxides of Group VIA and/or Group VIII deposited on a solid porous support, such as silica and/or metal oxides such as alumina, titania, zirconia or mixtures thereof. Representative Group VIA metals include molybdenum, chromium and tungsten and Group VIII metals include nickel, cobalt, palladium and platinum. These metal components are deposited, in the form of metals or metal oxides, on the indicated supports in amounts generally between about 0.1 and about 20 weight percent.

Reformates are produced by reforming straight-run, thermal or catalytically cracked naphthas. Preferably, the reformates used in the post reforming treatment of the invention have research octane numbers of 50 to 90, and are thus low octane severity reformates. Most preferably, the research octane numbers of the reformate feed is 70 to 90. In such reformates (of 50 to 90 research octane) little if any hydrocracking of $C_6$ and $C_7$ paraffins contained therein has occurred. Reforming of $C_6$ and $C_7$ paraffins is most difficult. In other terms, preferably the naphtha precursor of the reformate is preferably a paraffinic naphtha containing $C_6$–$C_7$ paraffins.

Dehydrocyclization and Reforming Conditions

The benzene and toluene production from isomer free hexane and heptane under dehydrocyclization conversion conditions are noted in Table I.

TABLE I

| | Conversion Conditions | | |
|---|---|---|---|
| | Temperature | WHSV $C_6$–$C_7$ | Total Pressure (Abs.) |
| Broad | 400° to 600° W. | 0.1 to 10.0 | 5 to 500 psi |
| Preferred | 450° to 550° C. | 0.3 to 2.5 | 15 to 150 psi |

The WHSV (weight hourly space velocity) in Table I refers to the hexane and/or heptane component of the feed, and the total pressures given are absolute pressures.

When reforming is undertaken over the platinum/tin catalyst in accordance with the invention, the temperature of reforming in accordance with the invention can range from 800° F. to 1100° F., generally being greater than about 900 F., preferably 900° F. (482° C.) to 1050° F.; the pressure will be from about 1 atmosphere to 500 psig, preferably from 30 psig to 250 psig; inlet $H_2$/hydrocarbon can be 10 or less, even zero (0) as discussed in the Examples (because of hydrogen production during reforming, there will be a hydrogen partial pressure in the unit); while the LHSV (liquid hourly space velocity) can be 0.1 to 20, preferably 0.1 to 10.

In one embodiment of the invention, reforming of the heavy naphtha fraction, boiling range of up to 400° F. is undertaken separately from the light naphtha fraction, by conventional reforming. As discussed above, conventional reforming may be semi-regenerative, cyclic or continuous. Process conditions in conventional reforming include pressures of about 0 to 500 psig, preferably, the pressures used herein range from 50–250 psig; temperatures of 800° to 1100° F.; $H_2$/HC molar ratios of 1 to 20:1 preferably of about 2:1 to about 6:1; LHSV of 0.1 to 20 $hr^{-1}$. Conventional reforming catalysts for this stage can include conventional reforming hydrogenation/dehydrogenation metals on aluminas. Those reforming hydrogenation/dehydrogenation metals include: platinum, platinum-rhenium; platinum with iridium, rhenium, rhodium or admixtures thereof; or platinum/tin. These hydrogenation/dehydrogenation metal combinations are on alumina and are chlorided; generally they are presulfided prior to use on feeds containing less than about 1 ppm sulfur.

Conventional reforming catalysts can be used. Conventional reforming catalysts are chlorided; generally, they are presulfided and used on feeds containing less than about 5 ppm sulfur, and preferably less than 1 ppm. They are often run on systems exhibiting low water (vapor) partial pressures. These catalysts can be platinum on alumina chlorided nd presulfided run at low water vapor partial pressures; platinum rhenium chlorided and run at low water (vapor) pressures; trimetallics on alumina in which each of the trimetallic components is selected from the group consisting of platinum, rhenium, iridium, and rhodium or platinum and tin on alumina, chlorided and run at low water vapor partial pressures.

Post Reforming Conditions

Reforming of the naphtha fraction to produce the reformates of 50 to 90 octane is undertaken by conventional reforming in semi-regenerative, cyclic or continuous units. Process conditions in reforming include pressures up to 500 psig; temperatures of 800° F. to 1100° F.; unit inlet $H_2$/HC molar ratios of 1 to 20 and LHSV of 0.1 to 20.0. Conventional reforming catalysts can be used. To produce low octane severity reformates, naphtha catalyst contact time and/or reaction temperature is reduced during reforming. That contact time can be reduced by decreasing the amount of catalyst which would be used in a unit lined-out to produce reformate of given octane. Alternatively, LHSV of the feed can be increased over that in the lined-out unit. Alternatively, if 3 units are manifolded as in the semi-regenerative process, product can be diverted after the second unit to by-pass the third unit.

In accordance with the invention the post reforming treatment of reformates having research octane of 50 to 90 includes subjecting that reformate to elevated temperature conditions in the presence of catalyst composition comprising a hydrogenation/dehydrogenation component and non-acidic tin microporous material described below.

In accordance with the invention, the post reforming treatment includes temperatures of at least about 800° F., ranging from 800° F. to 1100° F., generally greater than about 900° F., preferably 900° F. (482° C.) to 1050° F.; the pressure will be from about 1 atmosphere to 500 psig, preferably from 30 psig to 250 psig; inlet $H_2$/hydrocarbon (feedstock) ratios can be 10 or less, even zero (0) as discussed in the Examples (because of hydrogen production during reforming, there will be a hydrogen partial pressure in the unit); while the LHSV (liquid hourly space velocity) can be 0.1 to 20, preferably it is 0.1 to 10.

Catalyst of the Invention

The dehydrocyclization and reforming catalyst of the invention is a two component catalyst comprising a reforming hydrogenation/dehydrogenation component and tin containing non-acidic crystalline microporous material. Preferably, that material is a crystalline microporous tin silicate. The hydrogenation/dehydrogenation component can be those including platinum; platinum-rhenium; platinum with iridium, rhenium, rhodium or mixtures thereof, generally containing a platinum group metal; but preferably, it is platinum.

The amount of the reforming metal in the catalyst composition can range from 0.01 to 30 weight percent and preferably from 0.02 to 10 weight percent and most preferably from 0.05 to 5 weight percent.

The tin content of the crystalline microporous materials can range from 0.01 to 20 weight percent. Practically, the tin content will range from 0.1 to 10 weight percent.

The crystalline microporous tin containing materials of the invention are characterized by Si/Al ratios of at least 2. However, the silica:alumina ratio of the zeolite can be up to 1000, or greater. In a preferred embodiment the aluminum content of these materials is less than 0.1 weight percent and more preferably less than 0.02 weight percent.

The crystalline microporous tin containing material of the invention can contain other elements including boron, iron, chromium and gallium. The content of these other elements in the crystalline tin containing silicates can range from 0 to 10 weight percent.

The tin containing crystalline materials of the invention, described herein, are crystalline in the sense that they are identifiable as isostructural with zeolites by X-ray powder diffraction pattern.

The crystalline microporous tin containing material has an X-ray diffraction pattern which corresponds to a zeolite, SAPO, ALPO, etc.

In a preferred embodiment the pore size of the microporous crystalline tin containing silicates ranges from about 5 to about 8 Angstroms. In a preferred embodiment the microporous crystalline material containing tin exhibits the structure of ZSM-5, by X-ray diffraction pattern. The X-ray diffraction pattern of ZSM-5 has been described in U.S. Pat. No. 3,702,886 and RE 29,948 each of which is incorporated by reference herein.

The compositions comprising hydrogenation/dehydrogenation metal combined with the crystalline tin containing silicates do not exhibit any appreciable acid activity. These catalysts would meet the criteria of non-acidic catalysts described by Davis and Venuto, J. CATAL. Vol. 15, p. 363 (1969). Thus, a non-equilibrium mixture of xylenes are formed from either n-octane or each individual methylheptane isomer, with the octane yielding more o-xylene and 2-methyl-heptane yielding mostly m-xylene, at conversions between 10 and 60%.

When, as in embodiments herein, the crystalline tin dehydrogenation metal containing material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

One way of incorporating tin into the composition of this invention is by incorporation during the synthesis of the non-acidic crystalline microporous material. Alternatively, tin can be incorporated with the crystalline composition post-synthesis of the microporous crystalline material. The dehydrogenating metal can be incorporated during or after synthesis iof the microporous crystalline material. The dehydrogenating metal can be incorporated before, simultaneously with or after tin incorporation.

Alternatively, reverse procedures can be applied in which the dehydrogenation function is first introduced with subsequent tin incorporation. Stepwise preparation includes techniques of cocrystallization, impregnation, or exchange. Cocrystallization can be undertaken in a two phase system described in commonly assigned Ser. No. 878,555, filed June 26, 1986. Other elements such as boron, iron chromium, gallium, can also be included. Simultaneous incorporation includes the combination of tin with the dehydrogenation/hydrogenation function during synthesis (i.e., crystallization) or simultaneously after synthesis of the crystalline material.

A tin free material can be treated with tin compounds at elevated temperatures. Such treatments can be conducted so that the source of tin is either in the gaseous or the liquid phase including the aqueous phase (such as tin II). Alternatively, a tin free crystalline reactant can simply be impregnated with tin source and then calcined at temperatures above 400° C.

The tin free reactant can have high silica:alumina ratios or contain other elements such as boron, chromium, iron, and gallium. Reactants and products containing 0.1 weight percent or less aluminum are the preferred embodiments of the examples. In materials of the invention, all cation-exchangeable sites are occupied by non-hydrogen (non-proton) and by non-hydrogen precursors, such as $NH_4^+$. Specifically, such sites are occupied by $Na^+$, $K^+$, $Cs^+$ or admixtures thereof. The alkali metals serve to neutralize any acidity due to framework aluminum. The source of alkali metal cation can derive from cations incorporated during synthesis, in excess of the aluminum content thereof. Alternatively, one can treat the final product with a basic solution of an alkali metal hydroxide as a final step prior to use, as described for example in U.S. Pat. No. 4,652,360.

In a preferred embodiment, the non-acidic crystalline microporous tin containing silicates of the invention are treated with $Pt(NH_3)_4Cl_2$ in aqueous solution which has a pH of at least about 7 to incorporate the necessary platinum for catalyst composition formulation.

The non-acidic, crystalline, microporous, tin modifier and dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica.

Process Significance

The dehydrocyclization and reformate production processes produce a product of increased aromatic content and of increased octane value over that of the feed. More significantly, it allows for increased product liquid yields by eliminating byproducts of hydrocracking.

Integrating conventional reforming of paraffin naphthas with the post reforming process of the invention can result in significant octane gains. Post-processing of reformates from conventional semi-regenerative reformers operating at low octane severity (naphthene and high molecular weight paraffin conversion only) and reaction pressures of 200–500 psig could result in overall product yields comparable to new low pressure cyclic reforming processes. The process of the invention allows prior operation of the conventional reformer at low octane severity, such that the conversion of $C_6$ and $C_7$ paraffins—the most difficult of the fractions to reform—is minimal and thus could result in lower reforming catalyst aging rates.

EXAMPLE 1

Reforming studies were conducted both in glass and stainless steel reactors at atmospheric pressure. The naphthas used were pretreated $C_6/C_7$ Arab light naphthas. Reactor effluents were analyzed by on-line GC on a 30 m DB-1 column [yields reported below are accordingly $H_2$-free weight basis] and liquid products were recovered by cooling in a $CaCl_2$-ice bath. Research octane numbers were determined in the Mobil Research and Development Corporation Paulsboro Analytical Department.

The reforming of a hydrotreated Arab light naphtha, b.p. 180°–250° F., was studies at 1000° F. in nitrogen. The results are shown below:

| Catalyst | Pt/Sn-ZSM-5 | Pt/Sn-ZSM-5 |
|---|---|---|
| Sn-ZSM-5 Source | EXAMPLE 7 | EXAMPLE 8 |
| Temperature | 1000° F. | 1000° F. |
| Pressure | atm. | atm. |
| WHSV | 4.0 | 2.0 |
| $N_2/HC$ | 3 | 4 |

| Selected Feed Components | Products (GC area* percent) | |
|---|---|---|
| $C_1-C_4$ | 0 | 0.74% | 0.69% |
| $2MC_5$ | 9.35% | 5.75% | 5.31% |
| $3MC_5$ | 7.11% | 4.32% | 3.88% |
| $n-C_6$ | 24.22% | 3.27% | 5.13% |
| BENZENE | 2.12% | 24.35% | 24.83% |
| $2MC_6$ | 8.41% | 5.24% | 4.69% |
| $3MC_6$ | 7.22% | 3.90% | 3.52% |
| $n-C_7$ | 17.05% | 1.21% | 3.17% |
| TOLUENE | 3.23% | 21.62% | 24.21% |

Preferential shape-selective conversion of the normal paraffins relative to isoparaffins was observed.

EXAMPLE 2

An extended light naphtha reforming run was conducted over a 0.9% Pt/Sn-ZSM-5 catalyst produced in Example 7 in nitrogen at $N_2/HC=5$ and atmospheric pressure. The inlet temperature was 527° C., and this was increased incrementally to 550° C. WHSV was 1.35 initially, and then 1.0. Throughout the run, the liquid product was collected in a $CaCl_2$-ice bath at approximately $-40°$ C. Overall liquid recovery was 90–92 wt % of feed. The measured research octane ratings (RON clear) of the various fractions collected ranged from 97 after 1 day on stream to better than 92 after 12 days on stream.

EXAMPLE 3

The aromatization of a hydrotreated $C_6-C_7$ light naphtha was investigated over a 1.6% Pt/Sn-ZSM-5 [analysis of which indicated 1.6% Pt; 3.0Sn; 0.64Na and less than 59 ppm $Al_2O_3$] in hydrogen at a $H_2/HC$ ratio of 1 at atmospheric pressure and 1 WHSV. The temperature ranged from 520°–538° C. over a period of 14 days. Liquid products were recovered in better than 90 wt% yield based on feed. The RON's of the collected products were 97–98.

EXAMPLE 4

The above run, EXAMPLE 3, was continued at 20 psig and 538°–550° C. The liquid product recovered in 85 wt% yield after a total of 25 days on stream exhibited a RON of 97 and a MON (motor octane number) of 83.

EXAMPLE 5

A silica-bound extrudate Pt/Sn-ZSM-5 was prepared and used for naphtha reforming. A high silica tin-containing ZSM-5 was synthesized as described earlier. It contained 6.84% C, 0.61% N, 5.31% Sn, 0.0057% Al, 1.04% Na, and 79.9% $SiO_2$. The silica-bound extrudate, containing 35% silica binder, was prepared according to U.S. Pat. No. 4,582,815.

The dry extrudate was calcined in nitrogen at 1000° F., and then ion-exchanged with $Pt(NH_3)_4Cl_2$. The platinum-containing catalyst was then calcined in $O_2$ at 350° C. The final catalyst composition analyzed for 0.78% Pt, 3.66% Sn, 0.33% Na, and 0.23% $Al_2O_3$.

A pretreated $C_6/C_7$ light naphtha was reformed over the above catalyst in hydrogen at a $H_2/HC$ ratio of 1, at 1 WHSV, atmospheric pressure, and 538° C. The liquid product recovered in better than 90 wt% yield has a RON clear of 95.6.

EXAMPLE 6

A mixture of $C_6$-$C_9$ normal paraffins (25% $C_6$, 29% $C_7$, 25% $C_8$, and 20% $C_9$) was reformed over a Pt/Sn-ZSM-5 [analysis of which indicated 1.5% Pt; 2.7Sn; 0.63Na and 72 ppm $Al_2O_3$] catalyst in hydrogen at a $H_2/HC$ ratio of 1, at atmospheric pressure, 1 WHSV, and 538° C. The liquid product which was recovered in 84 wt% yield had a RON of 100.

EXAMPLE 7

The tin contining ZSM-5 sample used in Example 6, was synthesized by dissolving 0.69 g $Sn(II)SO_4$ in 170 g de-ionized water and then adding 3.39 g NaOH. To this was added 6.38 g tetrapropylammonium bromide. The mixture was transferred to a 300 ml stainless steel autoclave and 16.0 g of a low aluminum content silica gel (SPEX Ind.) was added with stirring. The hydrogel formed by this reaction mixture is described by the following mole ratios:

$$SiO_2/Sn : H_2O/Sn : OH^-/SiO_2 : Na^+/SiO_2 : TPA^+/SiO_2$$
$$75 : 40 : 0.30 : 0.35 : 0.10$$

The hydrogel was reacted at 160° C. for 5 days with stirring (400 rpm) before quenching. The resulting crystalline product was processed in the usual manner by filtering, washing, and drying. X-ray diffraction analysis of the product zeolite showed it to be 100% crystalline ZSM-5. SEM indicated an average crystal size greater than 2 microns.

EXAMPLE 8

A tin containing ZSM-5 sample was synthesized at a $SiO_2/Sn$ ratio of 38, a $Na^+/SiO_2$ ratio of 0.40, and a synthesis time of 3 days.

Tin incorporation was achieved during the zeolite synthesis, i.e., tin salts were added directly to the high silica ZSM-5 synthesis mixture. SEM data suggests that a significant portion of the tin is located outside of the large crystals formed (FIG. 1). Nevertheless, some tin must be inside the ZSM-5 crystals, since it modifies the selectivity of the platinum, which itself is intracrystalline.

Platinum was incorporated by ion-exchange of the calcined zeolites, probably, via exchange for sodium ions associated with internal silyloxy groups. The presence of intracrystalline (intrazeolitic) platinum was confirmed by the extremely low benzene hydrogenation rates (TON=4 min$^{-1}$ at 100° C.) measured for these catalysts.

EXAMPLE 9

This example (not per se part of the invention) illustrates one preparation of a suitable catalyst.

A tin-containing high silica ZSM-5 was synthesized by dissolving 0.69 g $Sn(II)SO_4$ in 170 g deionized water and then adding 3.39 g NaOH. To this was added 6.38 g tetrapropylammonium bromide. The mixture was transferred to a 300 ml stainless steel autoclave and 18.0 g of a low aluminum content silica gel (SPEX Ind.) was added with stirring. The hydrogel formed by this reaction mixture is described by the following mole ratios:

$$SiO_2/Sn = 75; \quad H_2O/Sn = 40; \quad OH^-/SiO_2 = 0.30$$
$$Na^+/SiO_2 = 0.35; \quad TPA^+/SiO_2 = 0.10$$

The hydrogel was reacted at 160° C. for 5 days with stirring (400 rpm) before quenching. The resulting crystalline product was processed in the usual manner by filtering, washing, and drying. X-ray diffraction analysis of the product zeolite showed it to be 100% crystalline ZSM-5.

The as-synthesized tin silicates were calcined first in nitrogen and then in air at 520° C. The calcined materials were ion-exchanged with aqueous $Pt(NH_3)_4Cl_2$ at room temperature; typically, 15-20 mg per gram silicate was used. The platinum tetramine-containing silicates were then calcined in oxygen to 350° C. at 0.5° C./min.

The catalyst analyzed for 0.92% Pt, 2.7% Sn, 0.89% Na, and 225 ppm $Al_2O_3$.

EXAMPLE 10

(Best Mode in Ser. No. 230,729))

The ability of the catalyst of Example 9 to aromatize n-heptane to toluene was assessed at 538° C. and 30 torr heptane in nitrogen at atmospheric pressure. Results are shown below. Data for Pt/B-ZSM-5 (not part of this invention) is included for comparion purposes.

| Catalyst | Conver. | $CH_4$ Yield | Toluene Yield | Toluene Sel. |
|---|---|---|---|---|
| Pt/SnZSM-5 | 97.7% | 0.3% | 95.4% | 97.7% |
| Pt/B-ZSM-5 | 94.7% | 19.6% | 28.6% | 30.2% |

The conversion of n-hexane over the catalyst of Example 1 was assessed at 538° C. and 150 torr hexane in nitrogen at atmospheric pressure. Using a flow rate of approximately 120 cc/min. over 84 mg of catalyst, one obtained 58% conversion of n-hexane, with a benzene selectivity of 55%.

EXAMPLE 11

Tin ZSM-5 silicate was synthesized in a static system at 300° F. 400 g 28.5% sodium silicate (Q-brand) was added to a solution of 60 g 50% tetramethylammonium chloride, 15 g $SnCl_4.5H_2O$, 30 g 98% $H_2SO_4$, and 60 g TPA+Br− in 2250 g water. The mixture was stirred and then placed in a polypropylene bottle in an autoclave for 5 days. The product was 85% crystalline ZSM-5 and consisted of large 5-10 micron crystals. In this and following preparations the zeolitic silicates produced were characterized as having at least one crystal dimension which was at least 0.5 microns; it analyzed for 80.4% $SiO_2$, 0.30% $Al_2O_3$, 3.78% Sn, 2.00% Na, 7.70% C, and 1.05% N.

EXAMPLE 12

Another tin containing ZSM-5 sample was synthesized by dissolving 0.69 g $Sn(II)SO_4$ in 170 g de-ionized water and then adding 3.39 g NaOH. To this was added 6.38 g tetrapropylammonium bromide. The mixture was transferred to a 300 ml stainless steel autoclave and 16.0 g of a low aluminum content silica gel (SPEX Ind.) was added with stirring. The hydrogel formed by this reaction mixture is described by the following mole ratios:

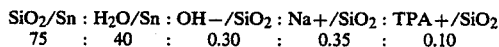

The hydrogel was reacted at 160° C. for 5 days with stirring (400 rpm) before quenching. The resulting crystalline product was processed in the usual manner by filtering, washing, and drying. X-ray diffraction analysis of the product zeolite showed it to be 100% crystalline ZSM-5. SEM indicated an average crystal size greater than 2 microns.

EXAMPLE 13

The effect of increasing the diluent:$H_2$ ratio in reforming is shown in the following example:

A model feed consisting of a 3:1 wt. ratio of n-heptane and methylcyclopentane was reformed over a non-acidic Pt/Sn-ZSM-5 catalyst containing 1.5% Pt, 2.7% Sn, 0.63% Na, and 72 ppm $Al_2O_3$. Conditions were 1 WHSV, 110 psig, and 538° C. The diluent ratios used were 4:1:1 $N_2$:$H_2$:HC and 6:1:1. The Figure below shows that when the diluent ratio was increased, the yield of aromatics (toluene) increased while the amount of residual unreacted heptane decreased. At the same time, loss to $C_1$-$C_5$ light hydrocarbons decreased from 6.5 wt% to 4.0 wt%.

EXAMPLE 14

Tin ZSM-5 species which can be used n catalyst composition of the invention are described in EXAMPLES 1–5.

Tin ZSM-5 silicate was synthesized in a static system at 300° F. 400 g 28.5% sodium silicate (Q-brand) was added to a solution of 60 g 50% tetramethylammonium chloride, 15 g $SnCl_4.5H_2O$, 30 g 98% $H_2SO_4$, and 60 g TPA+Br- in 2250 g water. The mixture was stirred and then placed in a polypropylene bottle in an autoclave for 5 days. The product was 85% crystalline ZSM-5 and consisted of large 5–10 micron crystals. In this and following preparation the zeolitic silicates produced were characterized as having at least one crystal dimenson which was at least 0.5 microns; it analyzed for 80.4% $SiO_2$, 0.30% $Al_2O_3$, 3.78% Sn, 2.00% Na, 7.70% C, and 1.05% N.

EXAMPLE 15

Another tin containing ZSM-5 sample was synthesized by dissolving 0.69 g Sn(II)$SO_4$ in 170 g de-ionized water and then adding 3.39 g NaOH. To this was added 6.38 g tetrapropylammonium bromide. The mixture was transferred to a 300 ml stainless steel autoclave and 16.0 g of a low aluminum content silica gel (SPEX Ind.) was added with stirring. The hydrogel formed by this reaction mixture is described by the following mole ratios:

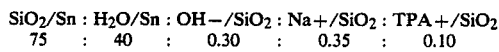

The hydrogel was reacted at 160° C. for 5 days with stirring (400 rpm) before quenching. The resulting crystalline product was processed in the usual manner by filtering, washing, and drying. X-ray diffraction analysis of the product zeolite showed it to be 100% crystalline ZSM-5. SEM indicated an average crystal size greater than 2 microns.

EXAMPLE 16

A tin containing ZSM-5 sample was synthesized in a similar manner except that the $SiO_2$/Sn ratio was 150 and the Na+/$SiO_2$ was 0.31. The crystalline ZSM-5 product contained 1.36% Sn, 0.0025% Al, 0.93% Na, and 89.31% Ash.

EXAMPLE 17

A tin containing ZSM-5 sample was synthesized in a similar manner except that the $SiO_2$/Sn ratio was 50, the Na+/$SiO_2$ was 0.38, and the synthesis time was 4 days.

EXAMPLE 18

A tin containing ZSM-5 sample was synthesized at a $SiO_2$/Sn ratio of 38, a Na+/$SiO_2$ ratio of 0.40, and a synthesis time of 3 days.

Tin incorporation was achieved during the zeolite synthesis, i.e, tin salts were added directly to the high silica ZSM-5 synthesis mixture. SEM data suggests that a significant portion of the tin is located outside of the large crystals formed. Nevertheless, some tin must be inside the ZSM-5 crystals, since it modifies the selectivity of the platinum, which itself is intracrystalline.

Platinum was incorporated by ion-exchange of the calcined zeolites, probably, via exchange for sodium ions associated with internal silyloxy groups. The presence of intracrystalline (intrazeolitic) platinum was confirmed by the extremely low benzene hydrogenation rates (TON=4 $min^{-1}$ at 100° C.) measured for these catalysts.

EXAMPLE 19

Platinum incorporation into the silicates of Examples 14–18 was undertaken. The as-synthesized tin silicates were calcined first in nitrogen and then in air at 520° C. The calcined materials were ion-exchanged with aqueous Pt($NH_3$)$_4Cl_2$ at room temperature; typically, 15–20 mg per gram silicate was used in a non-acidic aqueous medium. The platinum tetramine-containing silicates were then calcined in oxygen to 350° C. at 0.5 C/min.

Elemental analysis of the tin silicate of Example 3 after platinum incorporation indicated Pt=0.80%, Sn=1.54%, Al=31 ppm.

Elemental analysis of the tin silicate of Example 1 after platinum incorporation, Pt=0.65%, Sn=3.50%, Al=0.093%.

What is claimed is:

1. A process for reforming a naphtha feedstock of low octane value comprising contacting the feedstock, under reforming conditions, with a non-acidic catalyst composition consisting essentially of
    a reforming hydrogenation/dehydrogenation metal in combination with
    a non-acidic microporous crystalline material containing tin, and
    recovering a reformate having an octane value greater than that of the feedstock and having an aromatic content greater than that of the feed.

2. The process of claim 1, wherein said reforming metal comprises 0.1 to 20 weight percent of the catalyst and said tin comprises 0.05 to 20 weight percent of the combination.

3. The process of claim 1, wherein said reforming conditions further includes adding hydrogen to the feedstock.

4. The process of claim 1, wherein the naphtha feedstock comprises a light naphtha fraction of $C_6$ to 250° F. boiling range components.

5. The process of claim 1, wherein the naphtha feedstock is separated into at least two fractions including a fraction containing $C_6$–$C_7$ paraffins wherein said fraction is contacted with said catalyst.

6. The process of claim 5, wherein a second fraction of said two fractions is contacted with a conventional reforming catalyst.

7. The process of claim 1, wherein said non-acidic crystalline material is a microporous material which is isostructural with a zeolite, selected from the group consisting of ZSM-5, ZSM-11, ZSM-12, ZSM-20, ZSM-23, ZSM-48, ZSM-50, and zeolite beta.

8. The process of claim 1, wherein the microporous crystalline material zeolite is ZSM-5.

9. The process of claim 1, wherein the aluminum content of the non-acidic crystalline microporous material is less than 0.1 weight percent.

10. The process of claim 1, wherein the aluminum content of the non-acidic microporous crystalline material is less than 0.02 weight percent.

11. The process of claim 1, wherein the reforming metal is a Group VIII metal.

12. The process of claim 1, wherein the hydrogenation/dehydrogenation metal is a platinum group metal.

13. The process of claim 1, wherein the hydrogenation/dehydrogenation metal is platinum.

14. The process of claim 1, wherein the pressure of the reforming conditions ranges from 0 to 500 psig.

15. The process of claim 5 wherein the pressure of reforming ranges from 0 to 500 psig.

16. The process of claim 1, wherein the liquid yield exceeds the liquid yield of reforming undertaken in the presence of the tin free counterpart of the non-acidic crystalline microporous material.

17. The process of claim 5, wherein the liquid yield exceeds the liquid yield of reforming undertaken in the presence of the tin free counterpart of the non-acidic crystalline microporous material.

18. The process of claim 1, wherein the temperature of reforming ranges from 800° to 1100° F.

19. The process of claim 1, wherein the feedstock, prior to said contacting, is subjected to fractionation to remove the fraction boiling below about 150° F.

20. The process of claim 5, wherein the tmperature of reforming ranges from 800° to 1100° F.

21. The process of claim 15, wherein the temperature of reforming ranges from 800° to 1100° F.

22. The process of claim 1, wherein the feedstock is rich in $C_6$–$C_9$ normal paraffins.

23. The process of claim 21, wherein the feedstock is rich in $C_6$–$C_9$ normal paraffins.

24. A process for upgrading a naphtha comprising in combination:
providing a feedstream which is a paraffin rich naphtha;
contacting the feedstream with a non-acidic catalyst consisting essentially of a hydrogenation/dehydrogenation metal and a tin-containing non-acidic crystalline microporous material, under conditions including a temperature of from 800° F. to 1100° F., a pressure of about 0 to 500 psig, and LHSV of 0.1 to 20; and
cofeeding with said feedstream a mixture of hydrogen and diluent which is inert to aromatization under the conditions of the process wherein the hydrogen:hydrocarbon (feed) ratio (molar) ranges from 0.1 to 20 and wherein the diluent:hydrocarbon (feed) ratio (molar) ranges from 1 to 20;
and recovering a reformate of octane number and aromatic content greater than that of the feedstream and greater than that of the reformate produced in the absence of said diluent.

25. The process of claim 24, wherein the diluent is at least one hydrocarbon of 1 to 5 carbon atoms.

26. The process of claim 24, wherein the diluent is an aromatic.

27. The process of claim 24, wherein at least a portion of the reformate is recycled as diluent in said cofeeding.

28. The process of claim 24, wherein the naphtha is hydrotreated prior to reforming.

29. The process of claim 24, wherein the crystalline microporous material is characterized by a pore size the average diameter of which ranges from about 5 to about 8 Angstroms.

30. The process of claim 24, wherein the crystalline microporous material is isostructural to ZSM-5.

31. The process of claim 24, wherein said metal is platinum.

32. The process of claim 30, wherein said metal is platinum.

33. The process of claim 24, wherein said crystalline microporous material is isostructural with a zeolite.

34. The process of claim 33, wherein said zeolite is ZSM-5, ZSM-11, ZSM-12, ZSM-20, ZSM-23, ZSM-48 and ZSM-50.

35. The process of claim 24, wherein said crystalline microporous material is a SAPO or an ALPO.

36. The process of claim 24, wherein said crystalline microporous material is bound with silica.

37. The process of claim 24, wherein the diluent is nitrogen, helium, carbon dioxide.

38. The process of claim 24, wherein the diluent is predominantly propane and the hydrogen:hydrocarbon (feed) ratio (molar) is preferably less than 3:1 and the reactor total pressure is less than 150 psig.

39. A process for reforming naphthas comprising
providing a feedstream which is a $C_{6+}$ paraffin rich naphtha;
contacting the feedstream with a catalyst comprising a reforming hydrogenation/dehydrogenation metal and a tin containing non-acidic crystalline microporous material, in the presence of a diluent, under reforming conditions, and to increase the octane of the reformate produced and its aromatic content.

40. The process of claim 39, wherein said diluent is $C_1$–$C_5$ hydrocarbon.

41. The process of claim 39, wherein the diluent is methane, ethane, propane, butane, isobutane, pentane, $C_1$–$C_5$ hydrocarbons and combinations thereof.

42. The process of claim 39, wherein the diluent is helium, nitrogen, or carbon dioxide.

43. The process of claim 39, wherein the naphtha is hydrotreated prior to reforming.

44. The process of claim 39, wherein the crystalline microporous material is characterized by a pore size the average diameter of which ranges from about 5 to about 8 Angstroms.

45. The process of claim 39, which further includes recovering hydrogen.

46. The process of claim 39, wherein said crystalline microporous material is isostructural with a zeolite.

47. The process of claim 46, wherein said zeolite is ZSM-5.

48. The process of claim 39, wherein the diluent is an aromatic.

49. The process of claim 39, wherein the diluent is reformate which is recycled during said cofeeding.

50. A method for increasing the aromatic content of a reformate with a research octane in the range of 50 to 90 comprising
  providing said reformate of research octane of 50 to 90 containing $C_{6+}$ aliphatics and contacting said reformate with a non-acidic catalyst composition, at a temperature of at least about 800° F., at a pressure ranging from about 0 to about 500 psig, and at a liquid hourly space velocity (LHSV) ranging from 0.1 to 20; wherein said catalyst composition consisting essentially of a hydrogenation/dehydrogenation component and a tin containing non-acidic crystalline, microporous material;
  producing a product of research octane greater than that of the reformate and of aromatic components content greater than that of the reformate.

51. The method of claim 50, wherein the hydrogenation/dehydrogenation metal is platinum.

52. The method of claim 50, wherein the hydrogenation/dehydrogenation metal is selected from the group consisting of platinum, palladium, rhodium, rhenium, and mixtures thereof.

53. The method of claim 50, the reformate of research octane of 50 to 90 which contains $C_6$ and $C_7$ paraffins, which on contact with said catalyst are aromatized to $C_{6+}$ aromatics.

54. The method of claim 50, further including increasing the liquid yield of reforming, by subjecting a naphtha, under reforming conditions, with an acidic reforming catalyst to produce said reformate of research octane of 50 to 90 and containing said $C_{6+}$ aliphatics, and then undertaking said contacting.

55. The method of claim 50, wherein providing said reformate includes subjecting a naphtha with a reforming catalyst under reforming conditions until the research octane of the reformed product has reached 50 to 90.

56. The method of claim 50, wherein providing said reformate comprises contacting naphtha fraction under reforming conditions of temperature and pressure with a reforming catalyst which is effective to provide a reformate of 50 to 90 research octane containing a $C_{6+}$ paraffin fraction.

57. The process of claim 56, wherein said $C_{6+}$ paraffin fraction includes $C_6$ to $C_{10}$ paraffins.

58. The method of claim 50, wherein the non-acidic microporous crystalline material exhibits the X-ray diffraction pattern of a zeolite.

59. The process of claim 58, wherein the non-acidic, microporous crystalline material contains less than 0.1 weight percent aluminum.

60. The method of claim 50, wherein the non-acidic crystalline microporous material exhibits the X-ray diffraction pattern of ZSM-5.

61. The method of claim 50, wherein the dehydrogenation metal is a Group VIII metal.

62. The method of claim 50, wherein the dehydrogenation metal is a platinum group metal.

63. A process for manufacturing benzene, toluene, or mixtures thereof, said process comprising providing a feed comprising substantially isomer-free normal hexane, substantially isomer-free normal heptane, or mixtures thereof and contacting said feed under dehydrocyclization conditions of temperature, pressure and space velocity with a non-acidic dehydrogenation catalyst consisting essentially of a platinum group metal supported on a zeolite containing tin or indium, said zeolite having the crystal structure of ZSM-5, ZSM-11, ZSM-12, ZSM-23, ZSM-35, ZSM-38 or ZSM-48, and recovering said benzene, toluene or mixture thereof.

64. The process described in claim 1, wherein said conversion conditions include a temperature of about 400° C. to about 600° C., a pressure of 5 to about 500 psi (absolute) and a hexane and/or heptane WHSV of 0.1 to 10.0 and wherein said catalyst comprises 0.1 to 20 wt% of platinum group metal and 0.05 to 20 wt% of indium or tin.

65. The process of claim 64, wherein said zeolite contains less than about 0.1 wt% alumina.

66. The process of claim 63, wherein said feed contains one or more diluents selected from the group consisting of hydrogen gas, an inert gas, and an aliphatic hydrocarbon having one to five carbon atoms.

67. The process of claim 64, wherein said feed contains one or more diluents selected from the group consisting of hydrogen gas, an inert gas, and an aliphatic hydrocarbon having one to five carbon atoms.

68. The process of claim 65, wherein said feed contains one or morediluents selected from the group consisting of hydrogen gas, an inert gas, and an aliphatic hydrocarbon having one to five carbon atoms.

69. The process of claim 63, wherein said zeolite has the crystal structure of ZSM-5 and said metal is platinum.

70. The process of claim 64, wherein said zeolite has the crystal structure of ZSM-5 and said metal is platinum.

71. The process of claim 65, wherein said zeolite has the crystal structure of ZSM-5 and said group metal is platinum.

72. The process of claim 66, wherein said zeolite has the crystal structure of ZSM-5 and said group metal is platinum.

73. The process of claim 67, wherein said zeolite has the crystal structure of ZSM-5 and said platinum group metal is platinum.

74. The process of claim 68, wherein said zeolite has the crystal structure of ZSM-5 and said platinum group metal is platinum.

75. A process for manufacturing benzene or toluene or mixtures thereof, said process comprising, in combination:
  fractionally distilling a straight-run paraffinic gasoline and recovering a fraction rich in normal hexane or normal heptane or a mixture thereof;
  contacting said recovered fraction with a Type 5A molecular sieve whereby sorbing said normal paraffin or paraffins from said recovered fraction and recovering a substantially isomer-free normal paraffin or paraffins;
  and contacting under dehydrogenation conditions said substantially isomer-free normal paraffin or paraffins with a non-acidic dehydrogenation catalyst consisting essentially of a platinum group metal supported on a tin containing zeolite, said zeolite having the crystal structure of ZSM-5, ZSM-11, ZSM-12, ZSM-23, ZSM-35, ZSM-38 or ZSM-48.

* * * * *

UNITED STATES PATENT AND TRADEMARK OFFICE
CERTIFICATE OF CORRECTION

PATENT NO. : 4,935,566

DATED : June 19, 1990

INVENTOR(S) : Ralph M. Dessau, Randall D. Partridge, Ernest W. Valyocsik & James C. Vartuli It is certified that error appears in the above-identified patent and that said Letters Patent is hereby corrected as shown below:

Column 20, line 28; "morediluents" should be --more diluents--.

Signed and Sealed this

First Day of September, 1992

Attest:

DOUGLAS B. COMER

Attesting Officer

Acting Commissioner of Patents and Trademarks